United States Patent [19]

Moore

[11] Plant 4,254

[45] May 30, 1978

[54] MINIATURE ROSE PLANT

[76] Inventor: Ralph S. Moore, 2519 E. Noble Ave., Visalia, Calif. 93277

[21] Appl. No.: 829,510

[22] Filed: Aug. 31, 1977

[51] Int. Cl.[2] ..... A01H 5/00

[52] U.S. Cl. ..... Plt./7

[58] Field of Search ..... Plt./7

*Primary Examiner*—Robert E. Bagwill
*Assistant Examiner*—James R. Feyrer

[57] ABSTRACT

This invention relates to a new and distinct variety of miniature rose primarily distinguished by the orange and pink coloring of buds and flowers and by the "mossy growth" on the sepals.

1 Drawing Figure

1

The present invention relates to a new and distinct variety of hardy, dwarf, bush type rose plant of the miniature class; the variety being primarily characterized — as to novelty — by: (A) rich orange to orange-pink buds and flowers which in general color effect are similar to, but more yellow than Hula Girl (miniature — U.S. Plant Pat. applied for) and (B) by the "mossy" growth on sepals of buds and flowers The variety is further characterized by:

An abundance of bloom, with flowers borne singly or several to the stem in loose clusters.

Some fragrance.

A plant which is vigorous, of rounded, upright shape with small semi-glossy to matt foliage with pointed leaflets; the buds and flowers being similar in form and size to Golden Angel (miniature — U.S. Plant Pat. No. 4,028).

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Fairy Moss (U.S. Plant Pat. No. 3,083 — miniature) as the seed parent and Goldmoss (Floribunda Moss — U.S. Plant Pat. No. 3,562), as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature — Moss. Variety name: Mood Music.

Flowers borne: Singly and several together (three to five) on slender wirey stems.

2

Quantity of bloom: Abundant both outside and in greenhouse.

Bud: Peduncle — medium length; slender but sturdy; erect; medium green, sometimes tinted bronze (outdoors); with many prickles and small thorns. Before calyx breaks; size — small. Form long: pointed with numerous foliaceous apendages and numerous hairs and moss-like apendages on surface of bud; with foliaceous parts extending beyond the tip of the bud equal to one-half or less of its length. Color — medium green, occasionally tinted with bronze (outdoors). As calyx breaks, color — yellow, shading into orange or orange-pink on upper portion of bud. Opening: opens well in all weather.

Bloom: Size when fully open — small, averaging about 35–40 mm. Petalage — double — averaging about 55–60 petals, arranged regularly plus sometimes several small petaloids. Form — cupped at first becoming more high centered with petals rolled loosely outward and downward. Open flowers may show stamens.

Petals: Fairly thick; satiny on inside and on outside surface. Shape — outside petals, broad lanceolate (nearly round) with rounded tip; intermediate — broad lanceolate with acute or rounded tip; inside — lanceolate with acute tip.

Color: Newly opened flower from a plant grown in plastic greenhouse (August 1977), Visalia, Calif.:

*Outside petal.*—Outside surface — near Shrimp Red 616/2 becoming yellow to greenish yellow toward base. Inside surface — near Shrimp Red 616 or 616/1 becoming yellow toward base and more pink toward tip.

*Intermediate petal.*—Outside surface near Shrimp Red 616 (or more red) and shading into bright yellow near base. Inside surface near Mandarin Red 17/1 becoming bright yellow at base.

*Inner petal.*—Outside surface — same as intermediate petal; inside surface — same as intermediate petal. General color effect; newly opened flowers — bright orange to orange-pink. Three days open — color gradually changes to pink — near Azalea Pink 618/2. Behavior — open well in all weather. Spent petals drop off. Flower longevity (July – August 1977) — plant in pot 4–6 days or longer. Cut flowers at living room temperature 3–5 days.

Reproductive organs:

*Stamens.*—Sometimes present — arranged regularly about pistils.

*Filaments.*—Varying length, medium long, yellow.

*Anthers.*—If present — may or may not be well formed.

*Pollen.*—May be small amount.

*Pistils.*—Average number but may vary.

*Styles.*—If present — fairly even; medium length; bunched.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; medium small; leathery; semi-glossy to matt.

*Leaflets.*—Shape: broad, nearly oval; apex acute; base rounded. Margin serrate. Color: medium green; new growth — normal (medium) green (sometimes tinted reddish). Rachis: medium strength; upper side may have several thorns and tiny short prickles, grooved; underside may have several thorns and tiny short prickles. Stipules: Medium long; narrow to medium width; medium length narrow points which turn out usually at about 45° or more.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Numerous; slender; mostly straight; of varying size and length; color: brown. Prickles — several. Hairs — several.

*Branches.*—Color: medium green. Thorns: numerous varying length; slender; usually straight. Medium to short oval base. Prickles: numerous. Hairs — numerous.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit substantially as illustrated and described, characterized by (1) well mossed buds and (2) by buds and flowers of rich orange to orange pink color, the buds and flowers resembling Golden Angel (miniature — U.S. Plant Pat. No. 4,028) in size and shape; and further characterized by a plant which is vigorous and compact, with all shoots and branches quite thorny, the said plant being easy to propagate from cuttings or by budding, with an abundance of small to medium size semi-glossy foliage and an abundance of flowers borne singly or several to the stem in loose clusters.

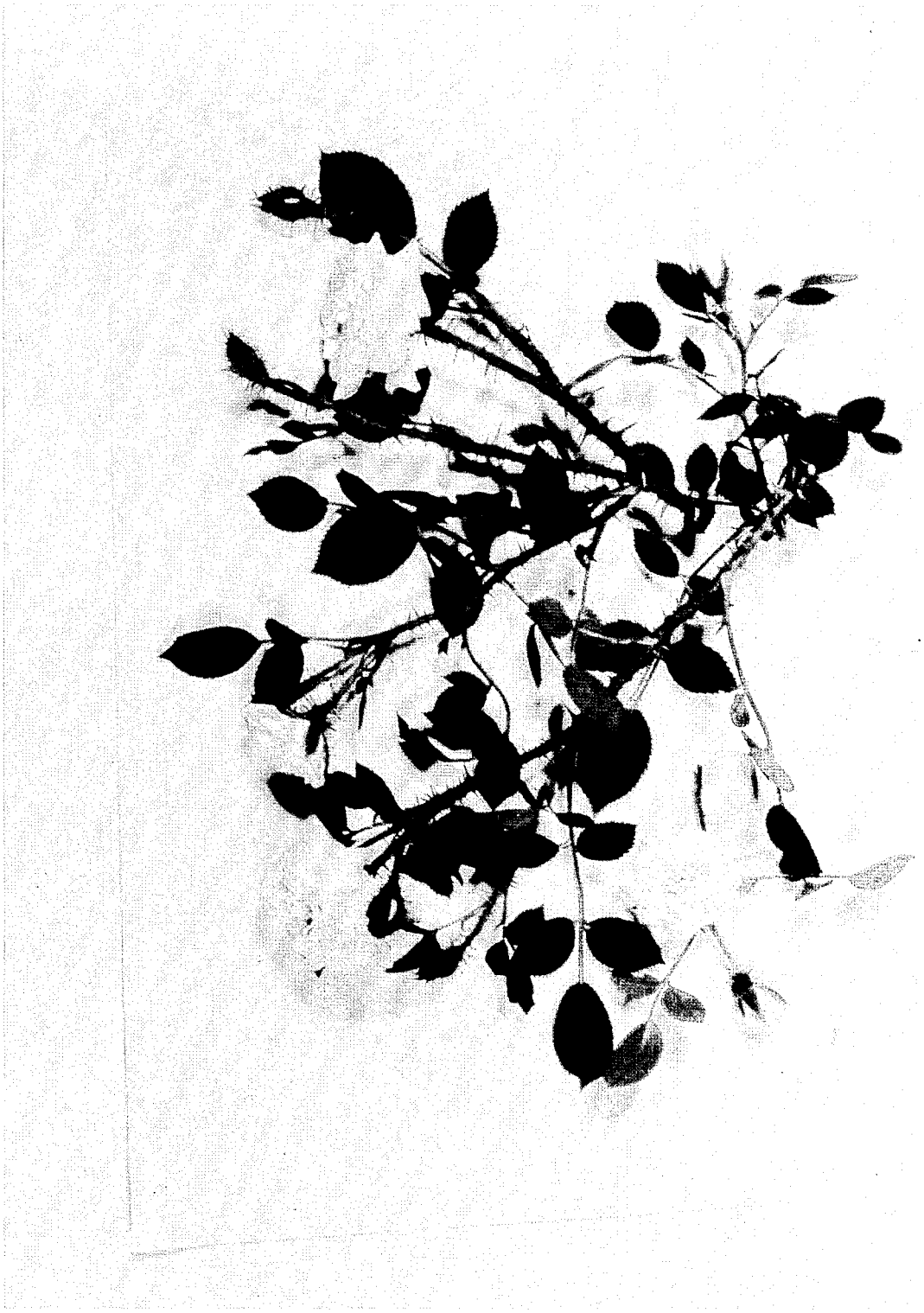

* * * * *